(12) United States Patent
Lillehoj et al.

(10) Patent No.: US 8,691,943 B2
(45) Date of Patent: Apr. 8, 2014

(54) ANTIMICROBIAL ACTIVITY OF CHICKEN NK-2 PEPTIDE AGAINST APICOMPLEXAN PROTOZOA

(75) Inventors: Hyun Soon Lillehoj, West Friendship, MD (US); Sung Hyen Lee, Laurel, MD (US); Yeong ho Hong, Geumjeong-dong Gunpo (KR)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 322 days.

(21) Appl. No.: 13/071,112

(22) Filed: Mar. 24, 2011

(65) Prior Publication Data

US 2012/0245082 A1 Sep. 27, 2012

(51) Int. Cl.
| | |
|---|---|
| *A61K 38/00* | (2006.01) |
| *C07K 5/00* | (2006.01) |
| *C07K 7/00* | (2006.01) |
| *C07K 16/00* | (2006.01) |
| *C07K 17/00* | (2006.01) |
| *A61K 38/04* | (2006.01) |
| *C07K 1/00* | (2006.01) |
| *A01N 37/18* | (2006.01) |
| *A61P 33/02* | (2006.01) |
| *A61K 51/00* | (2006.01) |

(52) U.S. Cl.
USPC .......... 530/324; 530/326; 530/350; 530/333; 530/344; 514/4.4; 514/1.1; 424/1.69

(58) Field of Classification Search
None
See application file for complete search history.

(56) References Cited

PUBLICATIONS

Hong et al. (2006) Vet. Immunol. ImmunopathoL 110: 339-347.*
Hong et aL 2008. Avian Dis. 52:302.305.*

* cited by examiner

*Primary Examiner* — Maury Audet
(74) *Attorney, Agent, or Firm* — John D. Fado; Evelyn M. Rabin

(57) ABSTRACT

NK-2 synthetic peptide derived from cationic core region of porcine NK-lysin has an antimicrobial and antitumor polypeptide that is considered to play a pivotal role in innate defense immunity. To evaluate the antimicrobial properties of synthetic chicken NK-lysin peptides, we investigated cytolytic activity against apicomplexan parasites like *Eimeria* sporozoites, *Neospora* tachyzoites and *Cryptosporidum* sporozoites. The chicken NK-2 (cNK-2) lytic peptide which corresponds to amino acid residues of porcine NK-2 peptide significantly disrupted *Eimeria* and *Cryptosporidum* sporozoites and *Neospora* tachyzoites. In contrast, no bactericidal activity was observed on *E. coli* BMH71-18. The cNK-2 lytic peptide is novel antimicrobial agent which can be used to intervene and treat economically costly infections in the animal industry.

5 Claims, 7 Drawing Sheets

```
                        SEQUENCE LISTING

<160> NUMBER OF SEQ ID NOS: 4

<210> SEQ ID NO 1
<211> LENGTH: 20
<212> TYPE: PRT
<213> ORGANISM: Gallus gallus

<400> SEQUENCE: 1

Gly Asp Asp Pro Asp Glu Asp Ala Ile Asn Asn Ala Leu Asn Lys Val
1               5                   10                  15

Cys Ser Thr Gly
            20

<210> SEQ ID NO 2
<211> LENGTH: 27
<212> TYPE: PRT
<213> ORGANISM: Gallus gallus

<400> SEQUENCE: 2

Arg Arg Gln Arg Ser Ile Cys Lys Gln Leu Leu Lys Lys Leu Arg Gln
1               5                   10                  15

Gln Leu Ser Asp Ala Leu Gln Asn Asn Asp Asp
            20                  25

<210> SEQ ID NO 3
<211> LENGTH: 22
<212> TYPE: PRT
<213> ORGANISM: Gallus gallus

<400> SEQUENCE: 3

Val Cys Ser Thr Gly Arg Arg Gln Arg Ser Ile Cys Lys Gln Leu Leu
1               5                   10                  15

Lys Lys Leu Arg Gln Gln
            20

<210> SEQ ID NO 4
<211> LENGTH: 30
<212> TYPE: PRT
<213> ORGANISM: Gallus gallus

<400> SEQUENCE: 4

Ala Ile Asn Asn Ala Leu Asn Lys Val Cys Ser Thr Gly Arg Arg Gln
1               5                   10                  15

Arg Ser Ile Cys Lys Gln Leu Leu Lys Lys Leu Arg Gln Gln
            20                  25                  30
```

ANTIMICROBIAL ACTIVITY OF CHICKEN NK-2 PEPTIDE AGAINST APICOMPLEXAN PROTOZOA

BACKGROUND OF THE INVENTION

1. Field of the Invention

This invention relates to the isolation and characterization of a novel lytic peptide, cNK-2, which is derived from chicken NK lysin and which has a direct killing activity against multiple *Eimeria* species as well as against other apicomplexa parasites including *Neospora* and *Cryptosporidia*.

2. Description of the Relevant Art

Avian coccidiosis is a ubiquitous intestinal protozoan infection of poultry seriously impairing the growth and feed utilization of infected animals. Conventional disease control strategies rely heavily on chemoprophylaxis resulting in high costs for the industry. However, due to the continual emergence of drug resistant strains of *Eimeria*, coupled with the increasing regulations and bans on the use of anticoccidial drugs in commercial poultry production, there is a need for novel approaches and alternative control strategies. Due to the complexity of the host immunity and the parasite life cycle, it has been difficult to develop new intervention strategies or recombinant vaccines against apicomplexa parasites.

NK-lysin has been characterized in mammalian as well as avian species (Andersson et al. 1995. *FEBS Lett.* 362:328-332; Davis et al. 2005. *Vet. Immunol. Immunopathol.* 105: 163-169; Endsley et al. 2004. *J. Immunol.* 173:2607-2614; Hong et al. 2006. *Vet. Immunol. Immunopathol.* 110: 339-347; Stenger et al. 1998. *Science* 282:121-125; Wang et al. 2006. *Fish Shellfish Immunol.* 20:419-426). NK-lysin in mammals, or granulysin in humans, is an antimicrobial and antitumor polypeptide expressed by NK cells and T lymphocytes. It possesses lytic activities against gram-positive and gram-negative bacteria, fungi and protozoan parasites (Andreu et al. 1999. *Biochem J.* 344 (Pt 3):845-849; Ernst at el. 2000.*J. Immunol.* 165:7102-7108; Gansert et al. 2003. *J. Immunol.* 170:3154-3161; Hong et al. 2008. *Avian Dis.* 52:302-305; Jacobs et al. 2003. *Antimicrob. Agents Chemother* 47:607-613; Stenger et al., supra). Antimicrobial peptides such as NK-lysin are widespread. More than 800 peptides have been identified from natural sources (Retrieved from the Internet: aps.unmc.edu/AP/main.php). However, only a very limited number of antimicrobial peptides are known to be effective against eukaryotic pathogens (Gelhaus et al. 2008. *Antimicrob. Agents Chemother.* 52:1713-1720).

Porcine NK-2, a shortened synthetic peptide comprising residues K39-K65 derived from the cationic core region of porcine NK-lysin with homologs in human and cattle, kills cancer cells as well as a variety of gram-negative and gram-positive bacteria, but exhibits no hemolytic or cytotoxic activity against human cells (Andra et al. 2004.*Antimicrob. Agents Chemother.* 48:1593-1599; Andra and Leippe. 1999. *Med. Microbial. Immunol.* 188:117-124; Schroder-Borm et al. 2005. *FEBS Lett.* 579:6128-6134). Moreover, porcine NK-2 peptide demonstrated that it disrupted the intracellular parasite *Trypanosoma cruzi* and intraerythrocytic *Plasmodium falciparum* (Gelhaus at al., supra; Jacobs et al., supra).

We have described the cloning and characterization of chicken NK-lysin, which exhibited anti-tumor cell activity against a retrovirus-transformed chicken B cell line and showed high cytotoxic activity against *Eimeria acervulina* and *E. maxima* sporozoites. However, no bactericidal activity was observed (Hong et al. 2006, 2008, supra).

There is a need for novel approaches and alternative strategies to control infections by apicomplexa parasites. *Eimeria* infects primarily the gut severely damaging its ability to absorb nutrition; whereas, *Neospora* and *Cryptosporidia* infect the gut of cattle and immunosuppressed humans. All three infections cause significant economic losses to the animal industry and there is no effective vaccines against them. Here, we have investigated the antimicrobial activity of synthetic chicken NK-lysin peptides against apicomplexan protozoa, in particular, *E. acervulina* sporozoites, *Neospora caninum* tachyzoites and *Cryptosporidum parvum*. Such peptide compositions permit the development of new treatment strategies.

SUMMARY OF THE INVENTION

We have identified a novel peptide within NK-lysin.

In accordance with this discovery, it is an object of the invention to provide a novel chicken NK-lysin peptide, cNK-2.

It is also an object of the invention to provide a therapeutic composition comprising a novel chicken NK-lysin peptide, cNK-2.

It is another object of the invention to provide a method for treating apicomplexa parasitic infection in animals by administering an effective amount of chicken NK-lysin peptide-2, cNK-2, to animals.

It is a further object of the invention to provide a method for treating *Eimeria* infection in chickens by administering an effective amount of chicken NK-lysin peptide-2, cNK-2, to chickens.

It is an additional object of the invention to provide a method for treating *Neospora* infection in mammals by administering an effective amount of chicken NK-lysin peptide 2, cNK-2, to mammals.

It is a still further object of the invention to provide a method for treating *Cryptosporidia* infection in mammals by administering an effective amount of chicken NK-lysin peptide 2, cNK-2 to mammals.

Other objects and advantages of this invention will become readily apparent from the ensuing description.

DETAILED DESCRIPTION OF THE INVENTION

Protozoan parasites in animals cause severe economic damages in animal productivity as well as animal health. In particular, coccidiosis caused by *Eimeria* spp. infection in poultry result in serious impairment of growth and feed utilization (Dalloul and Lillehoj. 2006. *Expert Rev. Vaccines* 5:143-163).

In previous studies, we demonstrated an anti-tumor effect of chicken NK-lysin, antimicrobial activity against *Eimeria* sporozoites and a lack of bactericidal activity (Hong et al. 2006, 2008, supra). The NK-2 cationic core region of porcine NK-lysin has been shown to have antimicrobial activity; NK-2 has cytotoxic activity against gram-positive and gram-negative bacteria (Andra et al., supra), intracellular parasite *Trypanosoma cruzi* (Jacobs et al., supra) and intraerythrocytic *Plasmodium falciparum* (Gelhaus et al., supra).

Here, synthetic NK-lysin peptides derived from a particular chicken NK-lysin amino acid sequence and covering helix 3 to 4 were evaluated. The cNK-2 lytic peptide is a natural product based on the NK-lysin protein which is secreted from chicken lymphocytes during coccidiosis and is highly effective against invasive stages of *Eimeria*. Unlike other drugs that have been used traditionally to control coccidiosis, chickens will not develop resistance against cNK-2 lytic peptide. The sequence of cNK-2 lytic peptide was designed and selected based on in vitro assays that we developed.

We have demonstrated that synthetic peptides derived from a particular chicken NK-lysin amino acid sequence are active against *Eimeria* sporozoites as well as other apicomplexan parasite like *Neospora* tachyzoites. The experiments clearly show that cNK-2 lytic peptide has cytolytic activity against *Eimeria acervulina* sporozoites (FIG. 1) and, in addition, cNK-2 lytic peptide showed cytolytic effects in other *Eimeria* spp. Synthetic cNK-2 lytic peptide caused membrane permeabilization in *E. maxima* and *E. tenella* (data not shown).

Figure 2:
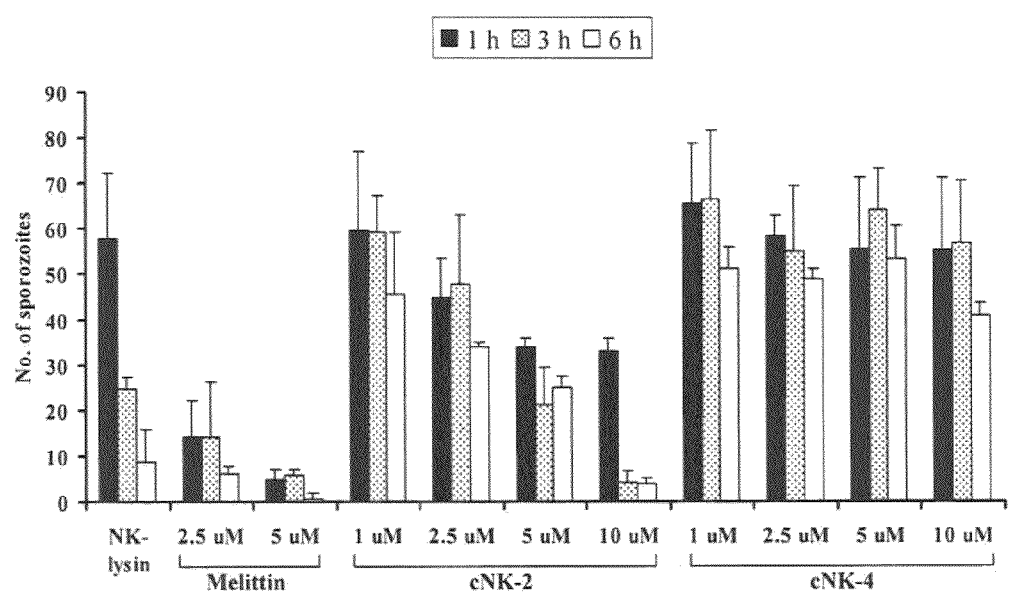
FIG. 2 shows time and peptide dependence of NK-lysin peptides to *Eimeria acervulina* sporozoites. For investigating the kinetics of NK-lysin peptides, *E. acervulina* sporozoites ($1.5 \times 10^6$/ml) were incubated with NK-lysin-transfected COS7 cell supernatant (1:1 dilution) and various concentrations of melittin, cNK-2 or cNK-4 for 1 h, 3 h and 6 h at 41° C.; sporozoite viability was assessed by trypan blue exclusion. Experiments were performed in triplicate.
Figure 3:
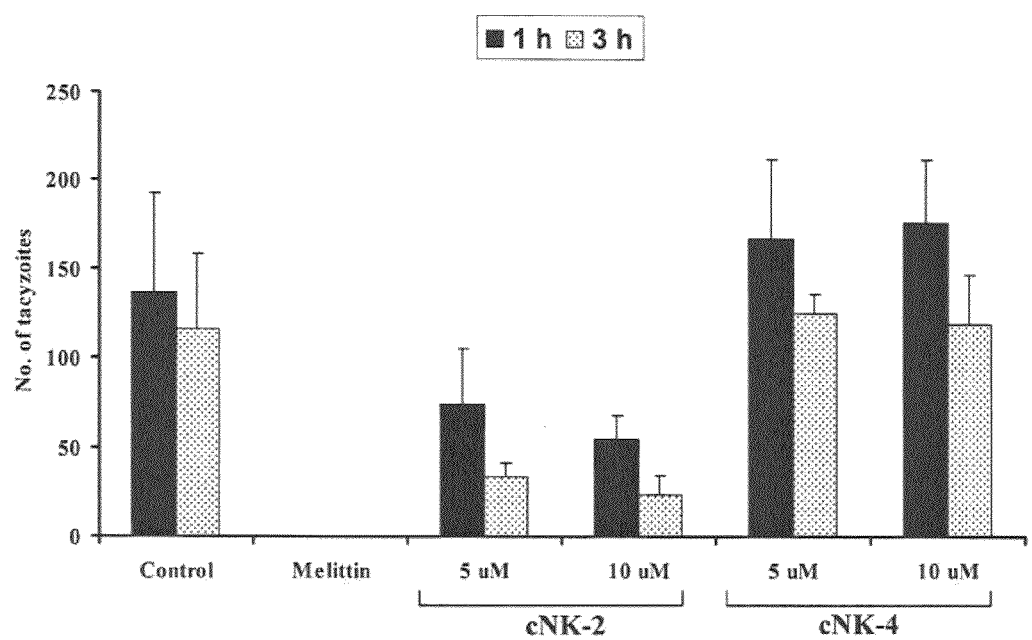
FIG. 3 depicts the dose- and time-dependant effects of chicken cNK-2 peptide on *Neospora caninum* tachyzoites. For investigating kinetics of NK-lysin peptides, *N. caninum* tachyzoites ($1.0 \times 10^7$/ml) were incubated with medium (control) and two different concentrations (5 uM and 10 uM) of cNK-2 for 1 h and 3 h at 41° C.; tachyzoite viability was assessed by trypan blue exclusion. Experiments were performed in triplicate. RPMI medium alone served as the negative control. Data were expressed as means±SEM. Differences were considered statistically significant at P<0.05 by the Duncan's multiple range test.

An important property of cytolytic peptides is the specificity for apicomplexan parasites, as demonstrated in FIGS. 2 and 3. This cNK-2 lytic peptide showed specific activity on apicomplexan parasites, namely, *Eimeria* sporozoites and *Neospora* tachyzoites. *Neospora* causes abortions in cattle. Up to 33% of pregnancies on one dairy farm can result in aborted fetuses. Therefore, it is clearly apparent that chicken NK-lysin plays an important role in intestinal innate immunity.

NK-lysin interacts with outer membrane lipids (lipopolysaccharides) of gram-negative bacteria and forms pores in the cell membrane due to its α-helical structure; however, this property is not generally sufficient for bacterial killing (Andersson et al. 1999. *Infect. Immun.* 67:201-205; Andreu et al., supra). Synthetic NK-lysin peptides, chicken NK-2 (cNK-2) and chicken NK-4 (cNK-4) did not inhibit the growth of *E. coli* BMH71-18. We had previously found that chicken NK-lysin had no bactericidal activity of against 16 bacterial strains (Hong et al., supra). Further, Linde et al. reported that a chicken synthetic peptide (cNKLF2) corresponding to the core sequence of chicken NK-lysin did not inhibit the growth of *E. coli* D2. However, bactericidal activity was observed against *B. megaterium* and *S. aureus* when a buffer-diluted medium was used instead of LB medium (Linde et al. 2005. *Infect. Immun.* 73:6332-6339).

At the cellular level, fluorescently-labeled porcine NK-2 peptide preferentially targets into parasite surface membranes with negatively charged phospholipids resulting in disruption of parasite membrane structure (Gelhaus et al., supra). Therefore, we explored the role of chicken NK-lysin in innate defensive immunity.

Synthetic chicken NK-lysin peptide, cNK-2, displays direct cytolytic activity against *Eimeria* sporozoites, *Neospora* tachyzoites, and *Cryptosporidum* sporozoites but has no bactericidal effects. cNK-2 lytic peptide is a highly interesting compound for development as a novel anti-parasitic agent and holds promise for pharmaceutical or agricultural uses in the animal industry.

A "protein" or "polypeptide" or "peptide" is a chain of amino acids arranged in a specific order determined by the coding sequence in a polynucleotide encoding the polypeptide. Each protein or polypeptide has a unique function.

The invention includes functional cNK-2 lytic peptide and functional fragments thereof, as well as mutants and variants having the same biological function or activity. As used herein, the terms "functional fragment", "mutant" and "variant" refers to a polypeptide which possesses biological function or activity identified through a defined functional assay and associated with a particular biologic, morphologic, or phenotypic alteration in the cell. The term "functional fragments of cNK-2" refers to all fragments of cNK-2 lytic peptide that retain cNK-2 lytic peptide activity and function to lyse *Eimeria* sporozoites and *Neospora* tachyzoites.

Modifications of the cNK-2 lytic peptide primary amino acid sequence may result in further mutant or variant proteins having substantially equivalent activity to the cNK-2 lytic peptide described herein. Such modifications may be deliberate, as by site-directed mutagenesis, or may occur by spontaneous changes in amino acid sequences where these changes produce modified polypeptides having substantially equivalent activity to the cNK-2 lytic peptide. Any polypeptides produced by minor modifications of the cNK-2 lytic peptide primary amino acid sequence are included herein as long as the biological activity of cNK-2 lytic peptide is present; e.g., having a role in pathways leading to lysis of *Eimeria* sporozoites and *Neospora* tachyzoites.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST. In general, a sequence of ten or more contiguous amino acids or thirty or more contiguous nucleotides is necessary in order to putatively identify a polypeptide or nucleic acid sequence as homologous to a known protein or gene. The instant specification teaches amino acid and nucleotide sequences encoding polypeptides that comprise a particular chicken protein. The skilled artisan, having the benefit of the sequences as reported herein, may now use all or a substantial portion of the disclosed sequences for purposes known to those skilled in this art. Thus, such a portion represents a "substantial portion" and can be used to establish "substantial identity", i.e., sequence identity of at least 80%, compared to the reference sequence. Accordingly, the instant invention comprises the complete sequences as reported in the accompanying Sequence Listing, as well as substantial portions at those sequences as defined above.

By "variant protein" a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein is intended. Variant proteins encompassed by the present invention are biologically active, that is they possess the desired biological activity, that is, cNK-2 lytic peptide activity as described herein. Such variants may result from, for example, genetic polymorphism or from human manipulation. Biologically active variants of a native chicken NK-lysin peptide of the invention will have at least about 90%, preferably at least about 95%, and more preferably at least about 98% sequence identity to the amino acid sequence for the native protein as determined by sequence alignment programs described elsewhere herein. A biologically active variant of a protein of the invention may differ from that protein by as few as 1-15 amino acid residues, or even 1 amino acid residue.

Methods of alignment of sequences for comparison are well known in the art. Thus, the determination of percent identity between any two sequences can be accomplished using a mathematical algorithm. Non-limiting examples of such mathematical algorithms are the algorithm of Myers and Miller (1988. *CABIOS* 4:11-17), the local homology algorithm of Smith et al. (1981. *Adv. Appl. Math.* 2:482); the homology alignment algorithm of Needleman and Wunsch (1970. *J. Mol. Biol.* 48:443-453); the search-for-similarity-method of Pearson and Lipman (1988. *Proc. Natl. Acad. Sci.* 85:2444-2448; the algorithm of Karlin and Altschul (1990. *Proc. Natl. Acad. Sci. USA* 87:2264), modified as in Karlin and Altschul (1993. *Proc. Natl. Acad. Sci. USA* 90:5873-5877).

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters.

As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins, it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule.

As used herein, "percentage of sequence identity" means the value determined by comparing two optimally aligned sequences over a comparison window, wherein the portion of the polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical amino acid residue occurs in both sequences to yield the number of matched positions, dividing the number of matched positions by the total number of positions in the window of comparison, and multiplying the result by 100 to yield the percentage of sequence identity.

As used herein, "reference sequence" is a defined sequence used as a basis for sequence comparison. A reference sequence may be a subset or the entirety of a specified sequence; for example, as a segment of a full-length protein sequence, or the complete protein sequence.

The polypeptides of the invention may be altered in various ways including amino acid substitutions, deletions, truncations, and insertions. Novel proteins having properties of interest may be created by combining elements and fragments of proteins of the present invention, as well as with other proteins. Methods for such manipulations are generally known in the art. Thus, the genes and nucleotide sequences of the invention include both the naturally occurring sequences as well as mutant forms. Likewise, the proteins of the invention encompass naturally occurring proteins as well as variations and modified forms thereof. Such variants will continue to possess the desired cNK-2 lysin activity.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays where the effects of cNK-2 lytic peptide can be observed.

The *Eimeria* and *Neospora* control compositions of the invention comprise the antimicrobial composition of the invention dissolved or suspended in an aqueous carrier or medium. The composition may further generally comprise an acidulant or admixture, a rheology modifier or admixture, a film-forming agent or admixture, a buffer system, a hydrotrope or admixture, an emollient or admixture, a surfactant or surfactant admixture, a chromophore or colorant, and optional adjuvants. The preferred compositions of this invention comprise ingredients which are generally regarded as safe, and are not of themselves or in admixture incompatible with human and veterinary applications. Likewise, ingredients may be selected for any given composition which are cooperative in their combined effects whether incorporated for antimicrobial efficacy, physical integrity of the formulation or to facilitate healing and health in medical and veterinary applications. Generally, the composition Comprises a carrier which functions to dilute the active ingredients and facilitates stability and application to the intended surface. The carrier is generally an aqueous medium such as water, or an organic liquid such as an oil, a surfactant, an alcohol, an ester, an ether, or an organic or aqueous mixture of any of these. Water is preferred as a carrier or diluent in compositions of this invention because of its universal availability and unquestionable economic advantages over other liquid diluents.

Avoiding the generalized use of broad range antimicrobials and using highly specific antimicrobials for just the target organisms involved, should help reduce the ever-increasing incidence of antibiotic resistance.

EXAMPLES

Having now generally described this invention, the same will be better understood by reference to certain specific examples, which are included herein only to further illustrate the invention and are not intended to limit the scope of the invention as defined by the claims.

Example 1

Peptide Synthesis

Four chicken NK-lysin peptides of 20- to 30-residues containing an amidated C-terminus were synthesized (Bio Basic Inc. Ontario, Canada) (Table 1). The peptides were obtained in a purity grade of more than 80%. Melittin (HPLC grade; Sigma-Aldrich, St. Louis, Mo.) was purchased as a synthetic positive control.

TABLE 1

Sequences of Synthetic Chicken NK-lysin Peptides.

| Peptides | Sequences | SEQ. ID NO. | M.W. (Da) |
|---|---|---|---|
| cNK-1 (81-101) | GDDPDEDAINNALNKVCSTG | 1 | 2047 |
| cNK-2 (101-127) | RRQRSICKQLLKKLRQQLSDALQNNDD | 2 | 3267 |
| cNK-3 (96-117) | VCSTGRRQRSICKQLLKKLRQQ | 3 | 2629 |
| cNK-4 (88-117) | AINNALNKVCSTGRRQRSICKQLLKKLRQQ | 4 | 3468 |

The position of synthetic peptide cNK-2 lytic peptide within the structure of NK-lysin is corresponding to amino acid residues with porcine NK-2 peptide. The antimicrobial activities of the synthetic chicken NK-lysin peptides were determined using *E. acervulina* sporozoites, *N. caninum* tachyzoites and *E. coli* strain BMH71-18.

Example 2

Antimicrobial Effects of NK-Lysin Peptides on *Eimeria* Sporozoites

*E. acervulina* sporozoites were obtained by excystation of sporulated oocysts (Dulski and Turner. 1988. *Avian Dis.* 32:235-239). After breaking the oocyst membrane with 0.5 mm glass beads by Mini-beadbeater (BioSpec Products Inc., Bartlesville, Okla.), sporocysts were purified by isopycnic centrifugation on a Percoll gradient, washed in cold PBS, then treated with excystation solution (0.25% trypsin, 0.014 M taurocholic acid) for 30 min at 41° C. to release sporozoites. Excystation fluid was filtered and the sporozoites were washed 3 times with cold HBSS at 3,000 rpm for 10 min at 4° C. and resuspended to $1.0 \times 10^6$/ml in HBSS or 10% RPMI-1640 medium (Sigma) (Hong et al. 2008, supra). The sporozoites were incubated for 1 h, 3 h or 6 h at 41° C. with NK-lysin-transfected COS7 cell supernatants, melittin or synthetic chicken NK-lysin peptides, stained with trypan blue, and viable sporozoites were counted microscopically.

Figure 1:
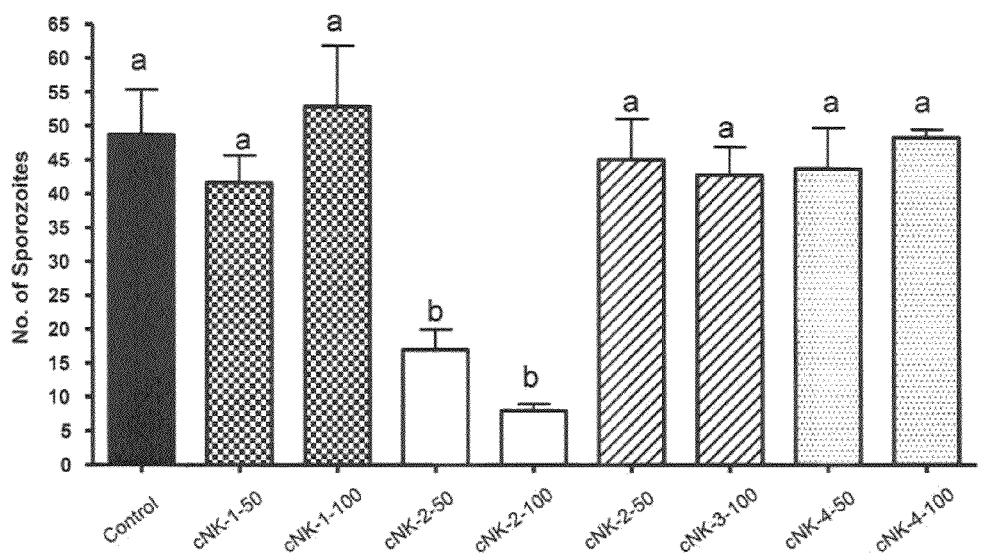
FIG. 1 depicts the cytotoxic activity of chicken NK-lysin peptides for *Eimeria acervulina* sporozoites. *E. acervulina* sporozoites ($2 \times 10^6$/ml) were incubated with control medium (HBSS) and 4 kinds of NK-lysin peptides (50 ug/ml, 100 ug/ml) for 3 h at 41° C. Sporozoite viability was assessed by trypan blue exclusion. Experiments were done in triplicate and considered significant at $P<0.01$.

To compare the effect of four kinds of chicken NK-lysin peptides on *Eimeria acervulina* sporozoites, *Eimeria* sporozoites were incubated in 50 μg/ml and 100 ug/ml of each peptide for 3 h at 41° C., respectively. The HBSS was used as a control. Only cNK-2 lytic peptide significantly killed *E. acervulina* sporozoites at 50 μg/ml or 100 μg/ml concentrations (P<0.01). In contrast, other peptides or control didn't kill *Eimeria* sporozoites (FIG. 1).

We next investigated the cytolytic activity of cNK-2 lytic peptide at increasing concentrations from 1 μM to 10 μM (FIG. 2). Melittin was used as a positive control to gain peptide-induced lysis in the absence of a phospholipid preference (Dempsey, C. E. 1990. *Biochim. Biophys. Acta* 1031: 143-161). Treatment with melittin at concentrations of 2.5 μM and 5 μM resulted in total disruption of the cellular membrane by breakdown of membranes into micelles in the manner of detergent solubilization. Incubation with 10 μM chicken NK-2 lytic peptide for 3 hr clearly had a time- and dose-dependent effect on *E. acervulina* sporozoites viability (FIG. 2), but no effect was seen with cNK-4 peptide. NK-lysin-transfected COS7 cell supernatants also showed cytolytic activity with time-dependence on *Eimeria* sporozoites.

Example 3

Antimicrobial Effects of NK-Lysin Peptides on *Neospora caninum* Tachyzoites

*N. caninum* tachyzoites were prepared as described with modifications (Tuo et al. 2005. *Infect. Immun.* 73:5093-5100). *N. caninum* (NC-1 isolate) tachyzoites were cultured on bovine monocytes (Lindsay and Dubey. 1989. *J. Parasitol.* 75:163-165) in RPMI 1640 medium supplemented with 2% fetal calf serum and 50 μg/ml gentamicin at 37° C. in a 95% air and 5% CO2 atmosphere. *N. caninum* tachyzoite-infected host cells were collected, passed through 20- and 27-gauge needles, and pelleted by centrifugation at 1,000×g for 20 min at 4° C. Tachyzoites were then purified by centrifugation over a 40% Percoll gradient at 2,000×g for 30 min at 4° C. The tachyzoite pellet was then resuspended in PBS (pH 7.4) and washed three times. Finally tachyzoites were resuspended to 5.0×10⁶/ml in 10% RPMI-1640 medium (Sigma). The tachyzoites were incubated for 1 h or 3 h at 41° C. with synthetic chicken NK-lysin peptides (5 μM and 10 μM), stained with trypan blue, and viable tachyzoites were counted microscopically.

We extended our target to the *N. caninum* tachyzoite which is an important coccidian parasite in cattle and dogs. After cNK-2 treatment of *N. caninum* tachyzoites, about 46 and 60% of tachyzoites are clearly killed at 5 uM and 10 uM cNK-2, respectively after a 1 h incubation (FIG. 3). After an incubation of 3 h, 71 and 86% killing were seen at 5 uM and 10 uM cNK-2, respectively.

Example 4

Antimicrobial Effects of NK-Lysin Peptides on *Cryptosporidum parvum* Sporozoites

*C. parvum* sporozoites were prepared as described with modifications (Riggs and Perryman. 1987. *Infect. Immun.* 55:2081-2087). The *C. parvum* sporozoites were incubated with various concentrations of cNK-2 peptides or BSA and viability was assessed after 2 hrs of incubation. Viability of the sporozoites was measured by a two-component fluorescent dye exclusion assay (LIVE/DEAD Reduced Biohazard Viability/Cytotoxicity Kits, Molecular Probes L-7013). Results are presented as the means plus standard deviations. Treatment with concentrations of cNK-2 (0.017, 0.17, 17 and 170 μg/ml) resulted in significant decreases in the viability of *C. parvum* sporozoites; $P<0.01$ at the 170 μg/ml concentration, as determined by the Student's t-test, the two factor factorial ANOVA Multiple comparison (Turkey, Scheffe's F-test and Bonferroni/Dunn), and Mann-Whitney's U test and $P<0.05$ at concentrations of 0.017, 0.17, and 17 μg/ml (Student's t-test). Statistical analysis was performed with the Statcel2 software.

Example 5

Bactericidal Effects of Chicken NK-Lysin Peptides

To evaluate the bactericidal activity of NK-lysin peptides, the minimum inhibitory concentration (MIC) values of the purified recombinant protein against *E. coil* strain BMH71-18 were determined using a standardized broth microdilution assay. Ampicillin MIC values against the bacteria were determined in parallel as positive controls. The assays were performed in accordance with Clinical and Laboratory Standards Institute (CLSI; Formerly National Committee for Clinical Laboratory Standards [NCCLS]) guidelines (NCCLS. 1999. In: *Methods for Determining Bacterial Activity of Antimicrobial Agents*, NCCLC, Wayne, Pa.; NCCLS. 2002. In: *Performance Standards for Antimicrobial Disk and Dilution Susceptibility Tests for Bacteria isolated from Animals; Approved Standard*, 2$^{nd}$ ed. NCCLS, Wayne, Pa.). Briefly, a single colony of bacterial inoculum was diluted in LB medium and the suspension adjusted to achieve a transmittance equivalent to a 0.5 McFarland standard (10⁸ CFU/ml) using a colorimeter. The bacterial suspension was diluted 100-fold in cation-adjusted Mueller-Hinton broth to 1.0×10⁶ CFU/ml. Fifty microliters was added to the wells of a 96-well round bottom plate containing 50 μl of either broth alone, or broth containing serially-diluted synthetic NK-lysin peptides or ampicillin (Sigma). A negative control consisted of 100 μl LB broth alone. The wells were incubated for 18 h at 37° C. with ambient air circulation and without shaking, and the optical density (OD) of each well was measured on a Synergy HT™ multi-modal plate reader (Bio-Tec Instruments, Winooski, Vt.) at 600 nm. Background values, derived from non-inoculated wells containing broth alone, were subtracted from all readings.

Figure 4:
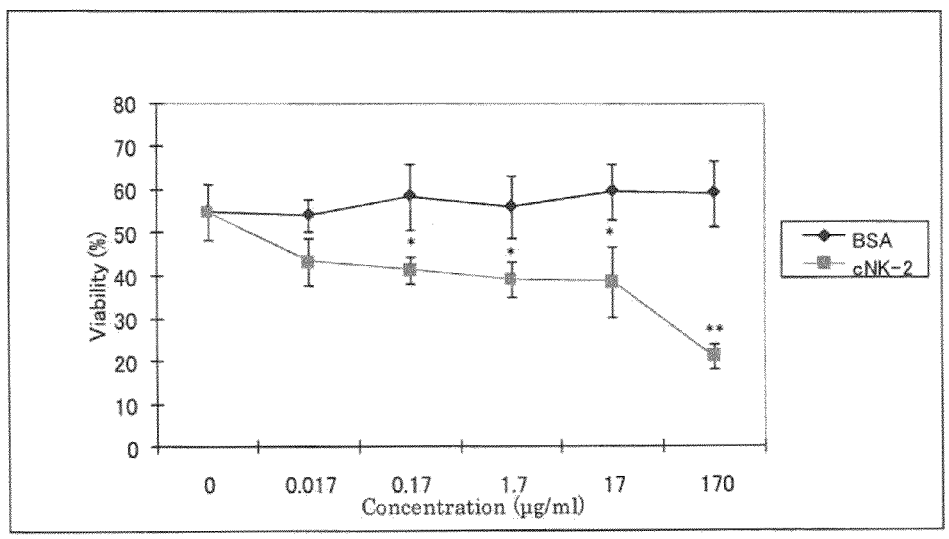
FIG. 4 depicts the effect of NK lysine on *Cryptosporidum parvum* sporozoites. Freshly prepared *C. parvum* sporozoites were incubated with different doses of cNK-2 for 3 hrs and *Cryptosporidia* sporozoite viability was measured by a two-component fluorescent dye exclusion assay (LIVE/DEAD Reduced Biohazard Viability/Cytotoxicity Kits, Molecular Probes L-7013). The result is presented as the means plus standard deviations. Statistical analysis was performed by the paired t-test with the Statcel2 software. The level of significance was set at a P value of <0.05.
Figure 5:
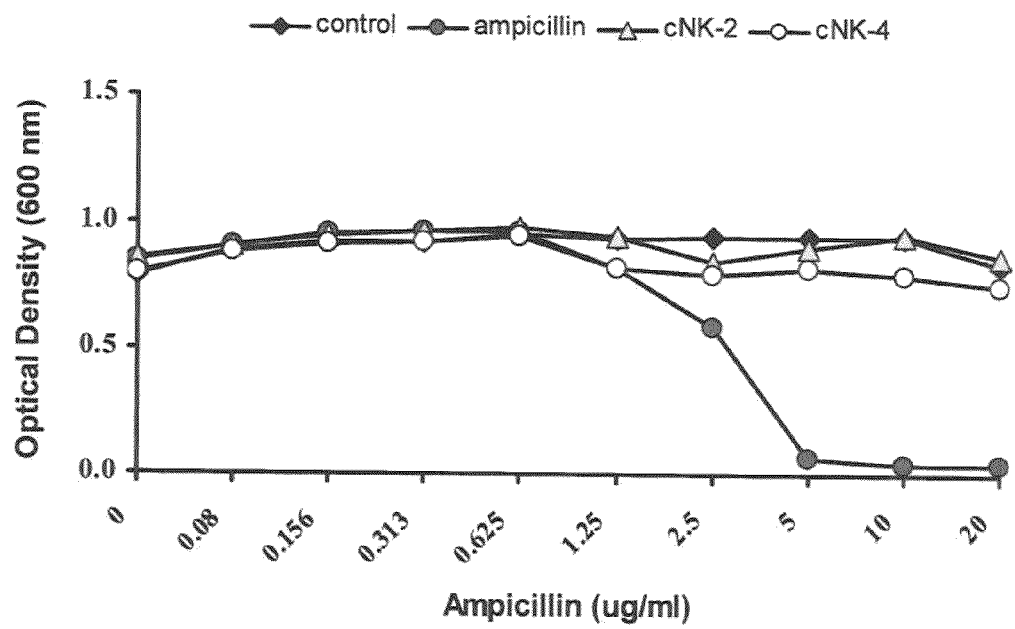
FIG. 5 shows the bactericidal activity of chicken NK-lysin peptides against *E. coli* BMH71-18 strain. Ampicillin (0-20 µg/ml), chicken NK-lysin peptides (0-40 µg/ml), or LB broth alone were added to cultures of the bacteria and incubated for 18 h at 35° C. Bacterial growth was determined by measuring $OD_{600}$. X axis: Ampicillin concentrations.

No bactericidal activity of NK-lysin, which was transfected into COS7 cell and expressed, was observed in previous report (Hong et al. 2008, supra). Neither chicken NK-lysin nor the NK-lysin peptides, cNK-2 and cNK-4, demonstrated antimicrobial activity against bacterial growth (FIG. 4). The MIC value of ampicillin against *E. coli* was 5-10 μg/ml.

Statistical Analysis: All data were analyzed with the Tukey's multiple comparison tests using Graphpad Prism 4 software (Graphpad, San Diego, Calif.) and considered significant at $P<0.01$.

Example 6

In ovo Administration of cNK-2 Peptide; Effect on Protection Against Live Oral Challenge Infection For protection studies, broiler eggs at the 18-day-old embryo stage were allocated into 4 groups of 12 eggs each. An in ovo injector was used to inoculate eggs. The two control groups (Groups 1 and 2) received no NK lysin peptide and were mock inoculated with Hanks Balanced Salt Solution (HBSS) only. Two groups were inoculated with an in ova injection of cNK-2 peptide (ARS005-1; RD-27) at doses of 1 μg/embryo (Group 3) or 5 μg/embryo (Group 4). Three days later, birds were hatched and moved to brooder petersime units. Birds of Groups 3 and 4 were given a second injection with cNK-2 peptide at doses of 1 μg/bird and 5 μg/bird, respectively, using an intraperitoneal route as shown in Table 2. Birds that had been injected in ova with HBSS alone were not given an additional intraperitoneal injection (Table 2).

At one day post hatch, the birds from Groups 2, 3 and 4 were challenged orally with 500 sporulated, live *Eimeria acervulina* oocysts. Body weights were measured at 1 day post hatch, i.e., on the day of challenge (coccidia infection), at 5 days (FIG. 6A) and at 10 days (FIG. 6B) post-infection.

TABLE 2

Experimental Design

| Group # | Group Name | No. of in ovo injections | Treatment Intraperitoneal | Infection with *E. acervulina* oocysts |
|---|---|---|---|---|
| 1 | HBSS | 12 | None | None |
| 2 | HBSS | 12 | None | 500 oocysts |
| 3 | cNK-2 peptide 1 μg | 12 | cNK-2 peptide 1 μg/100 μl | 500 oocysts |
| 4 | cNK-2 peptide 5 μg | 12 | cNK-2 peptide 5 μg/100 μl | 500 oocysts |

Figure 6A:
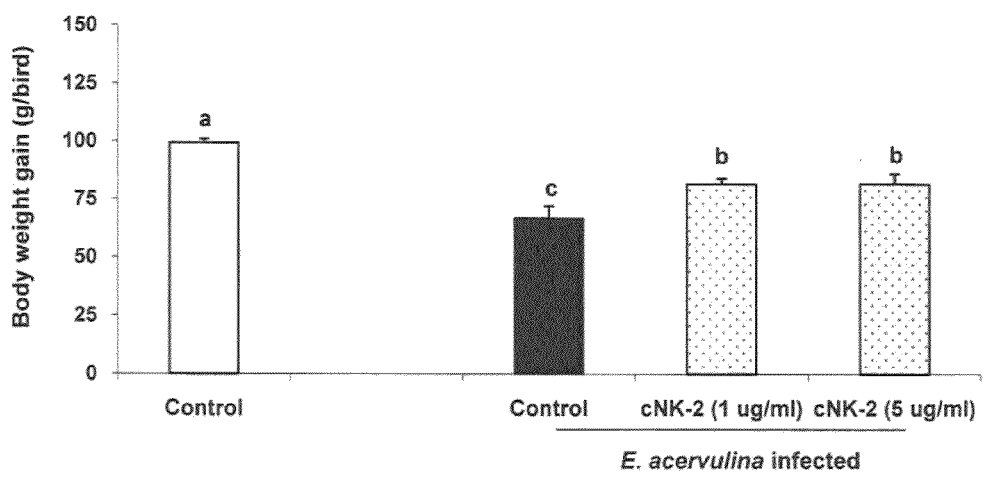
FIGS. 6A and 6B depict the effect of cNK-2 treatment on body weight gains of birds infected with *E. acervulina*. At 1 day post-hatch, the chickens were infected with 500 sporulated oocysts of *E. acervulina*. Body weights were assessed at 5 days (FIG. 6A) and 10 days (FIG. 6B) post-infection. Post infection, untreated control birds lost significantly more body weight compared with NK-lysin-treated groups. Birds receiving 1 µg and 5 µg cNK-2 peptide showed significantly higher body weights compared with control birds that received HBSS alone. Each bar represents the mean±SEM values. Bars not sharing the same letters are significantly different (P<0.05), according to the Duncan's multiple range test.
Figure 6B:
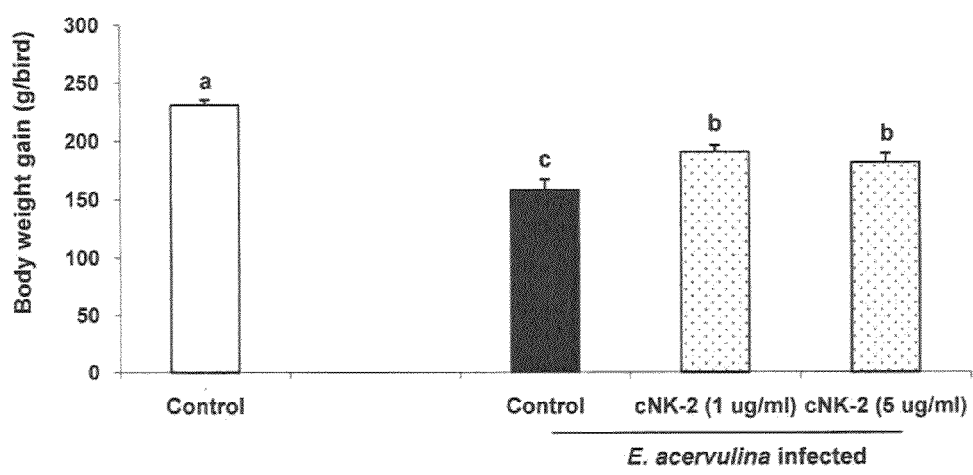

In ovo injections followed by intraperitoneal injections with cNK-2 peptide resulted in a significant protective effect against live oral challenge infection with *E. acervulina* oocysts. The treatment dose of cNK-2 peptide is important. The result of this trial showed that 1-5 μg level was effective to see body weight gain improvements (FIGS. 6A, 6B).

Figure 7:
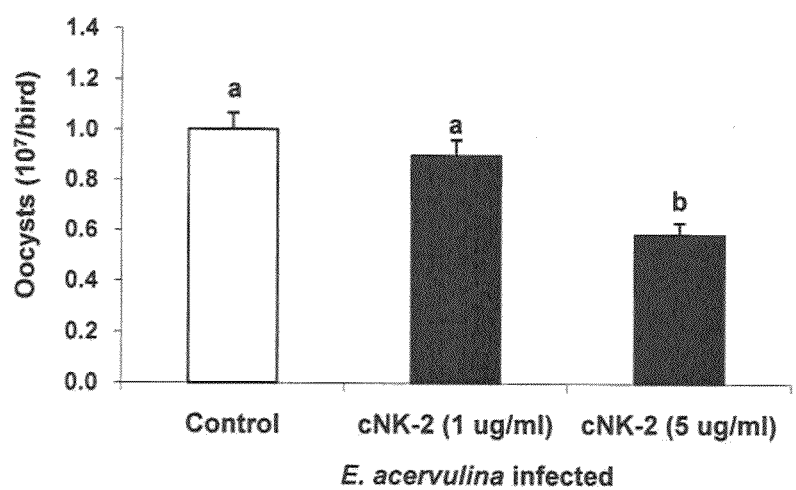
FIG. 7 depicts the effect of cNK-2 treatment on fecal oocyst shedding after oral challenge infection with live *E. acervulina*. At 1 day post-hatch, chickens were infected with 500 sporulated oocysts of *E. acervulina* and fecal oocysts were measured starting from day 5 to day 10 post-infection. Each bar represents the mean±SEM values. Bars not sharing the same letters are significantly different (P<0.05) according to the Duncan's multiple range test. Significant reduction of parasite shedding was seen in birds receiving 5 µg of cNK-2 treatment.

The effect of cNK-2 peptide on fecal oocyst shedding was also determined. As shown above, one day post hatch, the birds from Groups 2, 3 and 4 were challenged orally with 500 sporulated, live *E. acervulina* oocysts. Oocysts were collected between 5 and 10 days post infection and the number were counted using an established method (FIG. 7). A dose of at least 5 μg of cNK-2 was necessary to show significant reduction of fecal oocyst shedding. This is the first demonstration to show that a host-secreted anti-infective protein has a direct killing effect on coccidian parasites. These results indicate that chicken NK-2 peptide can replace anti-coccidial antibiotics.

Thus, this novel lytic peptide with specific action against apicomplexa parasites will enhance our ability to intervene and treat economically costly infections where conventional control methods are no longer effective. The new treatment strategies against *Eimeria* and other apicomplexa parasites, e.g., *Neospora caninum* and *Cryptosporidum parvum*, using the cNK-2 lytic peptide will have significant impact on the animal industry and will reduce consumers' concerns about poultry product-related drug resistance in humans.

All publications and patents mentioned in this specification are herein incorporated by reference to the same extent as if each individual publication or patent was specifically and individually indicated to be incorporated by reference.

The foregoing description and certain representative embodiments and details of the invention have been presented for purposes of illustration and description of the invention. It is not intended to be exhaustive or to limit the invention to the precise forms disclosed. It will be apparent to practitioners skilled in this art that modifications and variations may be made therein without departing from the scope of the invention.

We claim:

1. An novel isolated or synthesized chicken Natural Killer-2 (cNK-2) lytic peptide consisting of the amino acid sequence of SEQ ID NO: 2.

2. A therapeutic composition comprising the novel cNK-2 lytic peptide of claim 1 and a pharmaceutically acceptable carrier.

3. A method for treatment or protection against *Eimeria* infection in poultry in need thereof, comprising: administering an effective amount of a composition comprising an effective amount of the isolated or synthesized cNK-2 lytic peptide consisting of the amino acid sequence of SEQ ID NO: 2 to said poultry.

4. A method for treatment or protection against *Neospora* infection in a mammal in need thereof, comprising: administering an effective amount of a composition comprising an effective amount of the isolated or synthesized cNK-2 lytic peptide consisting of the amino acid sequence of SEQ ID NO: 2 to said mammal.

5. A method for treatment or protection against *Cryptosporidia* infection in a mammal in need thereof, comprising: administering an effective amount of a composition comprising an effective amount of the isolated or synthesized cNK-2 lytic peptide consisting of the amino acid sequence of SEQ ID NO: 2 to said mammal.

* * * * *